(12) United States Patent
Lenoble et al.

(10) Patent No.: US 6,399,579 B1
(45) Date of Patent: Jun. 4, 2002

(54) COMPOSITIONS COMPRISING ICARISIDE I AND ANHYDROICARITIN AND METHODS FOR MAKING THE SAME

(75) Inventors: Rod Lenoble; Steven L. Richheimer, both of Westminster; David Bailey, Boulder; Coralee G. Mannila, Monument; Rebecca L. Nichols, Broomfield, all of CO (US)

(73) Assignee: Hauser, Inc., Boulder, CO (US)

( * ) Notice: Subject to any disclaimer, the term of this patent is extended or adjusted under 35 U.S.C. 154(b) by 0 days.

(21) Appl. No.: 09/638,367

(22) Filed: Aug. 15, 2000

(51) Int. Cl.[7] .................. A61K 31/70; A61K 39/385
(52) U.S. Cl. .................. 514/25; 514/33; 424/195.1; 424/811; 536/8
(58) Field of Search .................. 514/25, 33; 424/195.1, 424/811; 536/8

(56) References Cited

PUBLICATIONS

Liang et al. "Isolation and immunomodulatory effect of flavonol glycosides from *Epimedium hunanense*." Planta Medica, 63, 316–319, 1997.*
Li et al. "Flavonol glycosides from *Epimedium Pubescens*." Journal of Nat. Prod., 53, 5, 1337–1339, 1990.*
Mizuno et al. "Flavonol glycosides in Epimedium Species." Chem. Pharm. Bull. 36, 9, 3487–3490, 1988.*
Li et al. "Flavonoids from *Epimedium wanshanense*." Phytochem. 43, 2, 527–530, 1996.*
Mizuno et al. "Flavonol glycoside from *Epimedium sagittatum*." Phytochem. 27, 11, 3641–3643, 1988.*
Mizuno, et al. "Flavonol Glycosides From *Epimedium Sagittatum*," *Phytochemistry,* (1988) 27: 3641–3643.
Mizuno, et al. "Flavonol Glycosides From *Epimedium Sagittatum*," *Phytochemistry,* (1987) 26:861–863.
Oshima, et al. "Epimedins A, B, And C, Flavored Glycosides of *Epimedium Korsanum* Herbs," (1987) 26.
*Oriental Materia Medica a Concise Guide,* "Herbs for Fever Rheumatism Digestive Problems Liver Ailments Detoxification Tonics & much more History and practice of Chinese Medicine" 563–565.
You–Ping Zhu, "Chinese Materia Medica," *Chemistry, Pharmacology and Applications* 596–602.

* cited by examiner

Primary Examiner—Ralph Gitomer
Assistant Examiner—Devesh Khare
(74) Attorney, Agent, or Firm—Steven C. Petersen; Sarah S. O'Rourke; Hogan & Hartson, LLP

(57) ABSTRACT

Compositions for maintaining normal sexual function and treating sexual dysfunction in males and females comprising at least 15% by weight icariside I or at least 3.5% by weight anhydroicaritin, derived from extracts of plants belonging the Epimedium genus, and methods for preparing the same, are provided. The methods comprise subjecting an Epimedium extract to mild acid hydrolysis. Methods for maintaining normal sexual function and treating sexual dysfunction in both males and females are also provided, comprising oral administration of an effective amount of a novel composition of this invention comprising at least 15% by weight icariside I or at least 3.5% by weight anhydroicaritin.

64 Claims, 8 Drawing Sheets

| Compound | $R^1$ | $R^2$ | |
|---|---|---|---|
| 1 | Glc | $Rha^2$—$^1$Glc | (epimedium A) |
| 2 | Glc | $Rha^2$—$^1$Xyl | (epimedium B) |
| 3 | Glc | $Rha^2$—$^1$Rha | (epimedium C) |
| 4 | Glc | Rha | (icariin) |
| 5 | H | $Rha^2$—$^1$Glc | (sagittatoside A) |
| 6 | H | $Rha^2$—$^1$Xyl | (sagittatoside B) |
| 7 | H | $Rha^2\!-\!^1Glc$, $3\!-\!Ac$ | (sagittatoside C) |

| Compound | R¹ | R² | |
|---|---|---|---|
| 1 | Glc | Rha²—¹Glc | (epimedium A) |
| 2 | Glc | Rha²—¹Xyl | (epimedium B) |
| 3 | Glc | Rha²—¹Rha | (epimedium C) |
| 4 | Glc | Rha | (icariin) |
| 5 | H | Rha²—¹Glc | (sagittatoside A) |
| 6 | H | Rha²—¹Xyl | (sagittatoside B) |
| 7 | H | Rha²—¹Glc, 3-Ac | (sagittatoside C) |

COMPOSITIONS COMPRISING ICARISIDE I AND ANHYDROICARITIN AND METHODS FOR MAKING THE SAME

BACKGROUND OF THE INVENTION

1. Field of the Invention

Compositions for maintaining normal sexual function and treating sexual dysfunction in males and females comprising at least 15% by weight icariside I or at least 3.5% by weight anhydroicaritin, derived from extracts of plants belonging the Epimedium genus, are provided. Methods for maintaining normal sexual function and treating sexual dysfunction in both males and females are also provided, comprising oral administration of an effective amount of a novel composition of this invention comprising at least 15% by weight icariside I or at least 3.5% by weight anhydroicaritin.

2. Description of the Prior Art

The most prevalent type of sexual dysfunction in males is "erectile dysfunction", e.g., "the inability to achieve and/or maintain an erection sufficient for sexual activity" (New England Journal of Medicine). Erectile dysfunction is most often attributable to the inability to generate enough NO in the corpus cavernosum.

The physiologic mechanism of erection of the penis involves release of nitric oxide (NO) in the corpus cavernosum during sexual stimulation. Nitric oxide then activates the enzyme guanylate cyclase, which converts guanosine triphosphate (GTP) to cyclic guanosine monophosphate (cGMP). cGMP in turn stimulates protein phosphorylation by cGMP-dependent protein kinase G, thereby producing smooth muscle relaxation in the corpus cavernosum and allowing inflow of blood. The cGMP is eventually metabolized by the enzyme phosphodiesterase type V (PDE-5). This enzyme can be inhibited by certain drugs, resulting in an increased concentration of cGMP.

Various inhibitors of phosphodiesterases are known, including sildenafil citrate (Viagra®). Viagra® is an oral drug for erectile dysfunction made by Pfizer, Inc. Viagra® is the citrate salt of sildenafil, a selective inhibitor of cyclic guanosine monophosphate (cGMP)-specific phosphodiesterase type V (PDE-5). Sildenafil enhances the effect of nitric oxide (NO) by inhibiting phosphodiesterase type V (PDE-5), which is responsible for degradation of cGMP in the corpus cavernosum. When sexual stimulation causes local release of NO, inhibition of PDE-5 by sildenafil causes increased levels of cGMP in the corpus cavernosum, resulting in smooth muscle relaxation and inflow of blood to the corpus cavernosum.

Although Viagra® has the potential to help millions of men, and some women, it is not a sexual cure-all. It is not an aphrodisiac and therefore will not work in the absence of desire. Viagra also produces a number of unpleasant side effects. These include headaches (10% of test subjects), seeing the color blue (3% of test subjects, blackouts due to sudden drops in blood pressure, priapism or prolonged erections beyond 4 hours, and coital coronaries.

It would also be advantageous to provide a composition as described above which is effective for treating sexual conditions in females. It has been found that clitoral smooth muscle cells include many of the same morphological characteristics as the male corpus cavernosum, and should be physiologically responsive via the same messengers (cGMP) to promote smooth muscle relaxation (Park et al., Journal of Urology, v. 159, (Jun. 1998)). Thus, that which promotes smooth muscle relaxation in the corpus cavernosum, allowing inflow of blood, and alleviating erectile dysfunction, should work well to alleviate female sexual dysfunction. Indeed, women claim to experience benefit from Viagra® and clinical tests are now being performed.

Extracts of plants of the genus Epimedium have been used for centuries, particularly in traditional Chinese medicine, as aphrodisiacs and have been used to treat sexual dysfunction in males. Scientific studies have shown that when an extract of the leaves of *Epimedium sagittatum* is administered orally to laboratory animals, the frequency of copulation increases significantly. Another mode of action of Epimedium extracts is to dilate capillaries and other blood vessels, thereby facilitating circulation to the sexual organs as well as the brain.

A number of constituents contained in the aerial parts of Epimedium species have been isolated and characterized. The constituents of Epimedium have been reported as flavonoids, alkaloids, and lignans. Mizuno et al. (*Phytochemistry* (1987) 26:861–863; and *Phytochemistry* (1988) 27:3641–3643) have reported the presence of icariside I in extracts of *Epimedium sagittatum*. However, to the best of the inventors' knowledge, there has been no study of the active components or metabolite(s) of Epimedium extracts which produce the desired effect of alleviating sexual dysfunction, nor have Epimedium extracts or any of the components of such extracts been evaluated for PDE-5 activity.

SUMMARY OF THE INVENTION

The present invention provides compositions enriched for icariside I and methods of obtaining such compositions from extracts of plants of the Epimedium genus. More specifically, the method of the present invention provides compositions comprising at least 15% by weight icariside I and methods for preparing the same.

A further object of this invention is to provide a method for producing compositions enriched for anhydroicaritin.

A further object of this invention is to provide compositions comprising at least 3.5% by weight anhydroicaritin.

A further object of the present invention is to provide a composition that is a PDE-5 inhibitor, wherein the composition comprises at least 15% by weight icariside I.

Another object of the present invention is to provide a composition that is a PDE-5 inhibitor, wherein the composition comprises at least 3.5% by weight anhydroicaritin.

Yet another object of this invention is to provide a method of inhibiting PDE-5 comprising administering to a subject an effective amount of a composition of this invention.

Further, the invention relates to methods and formulations for effectively treating sexual dysfunction or maintaining normal sexual function in males and females by orally administering a composition of this invention.

To achieve the foregoing and other objects and in accordance with the purposes of the present invention, as embodied and broadly described therein, one embodiment of this invention comprises a method of converting prenylated flavonol glycosides that are glycosylated at both the 3-position and the 7-position to a single compound, namely icariside I. More specifically, one embodiment of this invention comprises subjecting an Epimedium extract to mild acid hydrolysis to convert prenylated flavonol glycosides that are glycosylated at both the 3-position and the 7-position to one compound, namely icariside I. More specifically, one embodiment of this invention comprises a method of selectively hydrolyzing the 3-position glycoside units of compounds such as epimedium A, epimedium B, epimedium C, icariin, and their corresponding acetate derivatives without removing the 7-position glycoside of such compounds, to convert substantially all of such compounds present in the crude extract to icariside I. The resulting compositions obtained after mild acid hydrolysis according to the method of this invention comprise between about 15–60% by weight icariside I. The compositions obtained after acid hydrolysis are preferably purified to remove glycoside by-products and unreacted prenylated flavonol glycosides to yield compositions comprising between 15–60% by weight icariside I.

To further achieve the foregoing and other objects and in accordance with the purposes of the present invention, as embodied and broadly described therein, another embodiment of this invention comprises a method of producing a composition enriched in anhydroicaritin, the method comprising subjecting an Epimedium extract to mild acid hydrolysis to convert prenylated flavonol glycosides that are glycosylated at the 3-position and contain a hydroxyl group at the 7-position to one compound, namely anhydroicaritin. More specifically, one embodiment of this invention comprises a method of producing a composition enriched for anhydroicaritin, comprising subjecting an Epimedium extract to mild acid hydrolysis to hydrolyze the 3-position glycoside units of sagittatoside A, sagittatoside B, sagittatoside C, and the corresponding acetate derivatives to anhydroicaritin.

To further achieve the foregoing and other objects and in accordance with the purposes of the present invention, as embodied and broadly described therein, another embodiment of this invention comprises (1) subjecting an Epimedium extract to mild acid hydrolysis whereby the 3-position glycoside units of compounds such as epimedium A, epimedium B, epimedium C, icariin, and their corresponding acetate derivatives are selectively hydrolyzed to convert such compounds to icariside I, and the 3-position glycoside units of compounds such as sagittatoside A, sagittatoside B, sagittatoside C, and the corresponding acetate derivatives are hydrolyzed to convert such compounds to anhydroicaritin, thereby producing a composition enriched in icariside I and anhydroicaritin, and (2) subjecting this composition to enzymatic hydrolysis to hydrolyze the 7-position glycoside of icariside I to anhydroicaritin, thereby producing a composition further enriched in anhydroicaritin.

Other objects, features, and advantages of the present invention will become apparent from the following detailed descriptions. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The accompanying drawings, which are incorporated in and form a part of the specification, illustrate the preferred embodiments of the present invention, and together with the descriptions serve to explain the principles of the invention. In the Drawings.

DETAILED DESCRIPTION OF THE INVENTION

The present invention relates to compositions comprising icariside I, and to a novel, one step method of preparing such compositions, comprising converting specific prenylated flavonol glycosides such as epimedium A, epimedium B, epimedium C, icariin, and their corresponding acetate derivatives contained in an Epimedium plant extract to a single compound, namely icariside I shown below as compound I, which was surprisingly discovered to be a strong PDE-5 inhibitor.

I

This invention further comprises compositions enriched for anhydroicaritin, and to methods of preparing such compositions. One method of this invention for preparing compositions enriched for anhydroicaritin comprises a one-step method of converting prenylated flavonol glycosides, specifically the sagittatoside compounds A, B, and C, and the corresponding acetate derivatives, present in Epimedium plant extracts to a single compound, namely anhydroicaritin shown below as compound II, which was also discovered to be a strong PDE-5 inhibitor.

II

Yet another method for preparing compositions enriched for anhydroicaritin comprises subjecting a composition comprising icariside I to enzymatic hydrolysis, thereby converting substantially all of the icariside I to anhydroicaritin.

Figure 1:
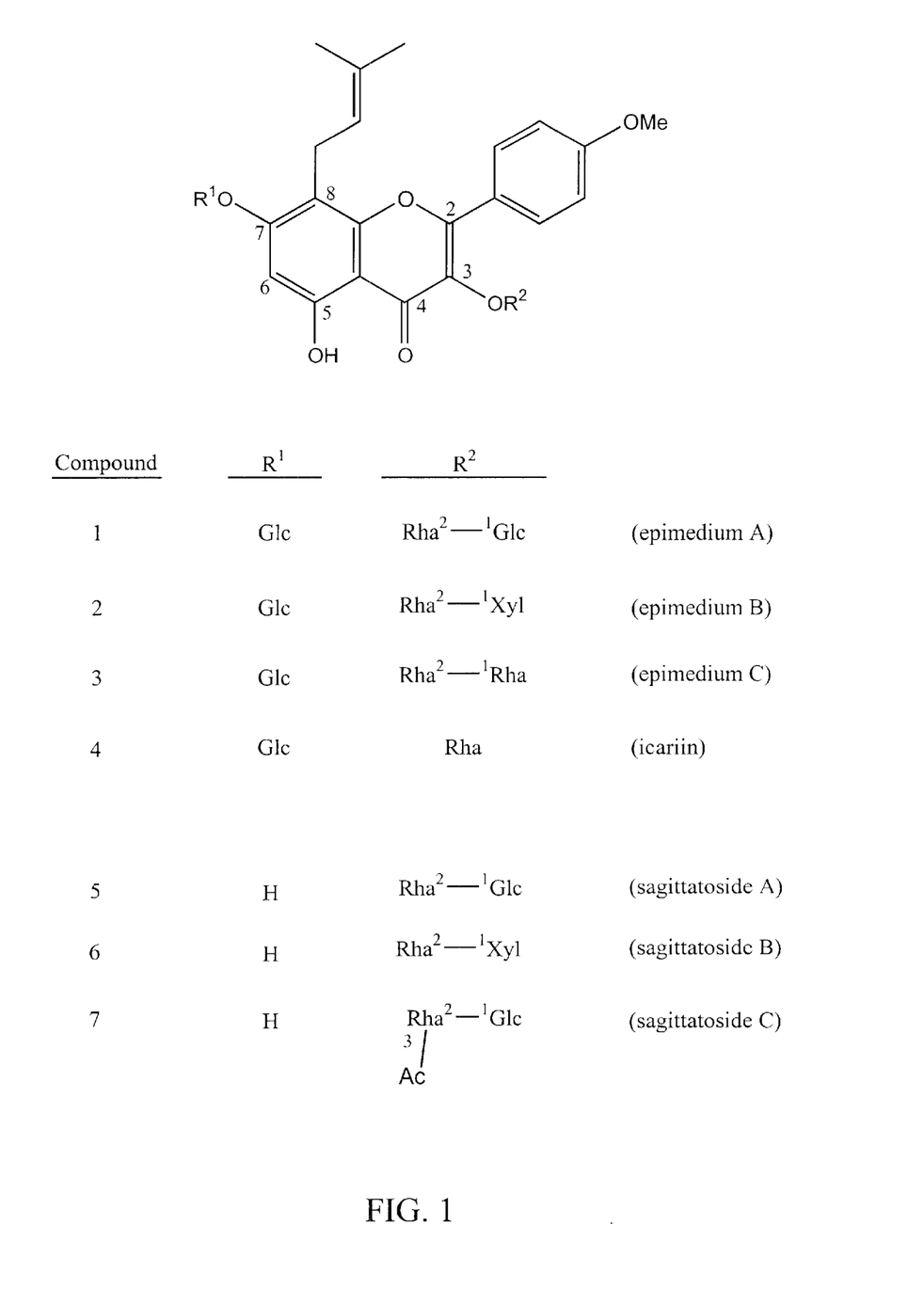
FIG. 1 shows examples of prenylated flavonol glycosides contained in Epimedium plants.

Plants of the Epimedium genus, particularly the leaves and stems of such plants, are known to contain a number of prenylated flavonol glycosides (PFG's) such as compounds 1–7 shown in FIG. 1, which can be generally grouped into two categories. Group I comprises prenylated flavonol glycosides that are glycosylated at both the 3-hydroxyl position and the 7-hydroxyl position. Group I compounds include, but are not limited to, compounds such as epimedium A (1), epimedium B (2), epimedium C (3), and icariin (4). Group II comprises prenylated flavonol glycosides that are glycosylated only at the 3-hydroxyl position. Group II compounds include, but are not limited to, compounds such as sagittatoside A (5), sagittatoside B (6), and sagittatoside C (7). In addition, acetate derivatives of compounds 1–7 are often present in plants of the Epimedium genus. As used herein, the term "acetate derivative" refers any derivative of compounds 1–7 containing an acetyl group in place of one or more of any hydroxyl group of compounds 1–7.

Figure 2:
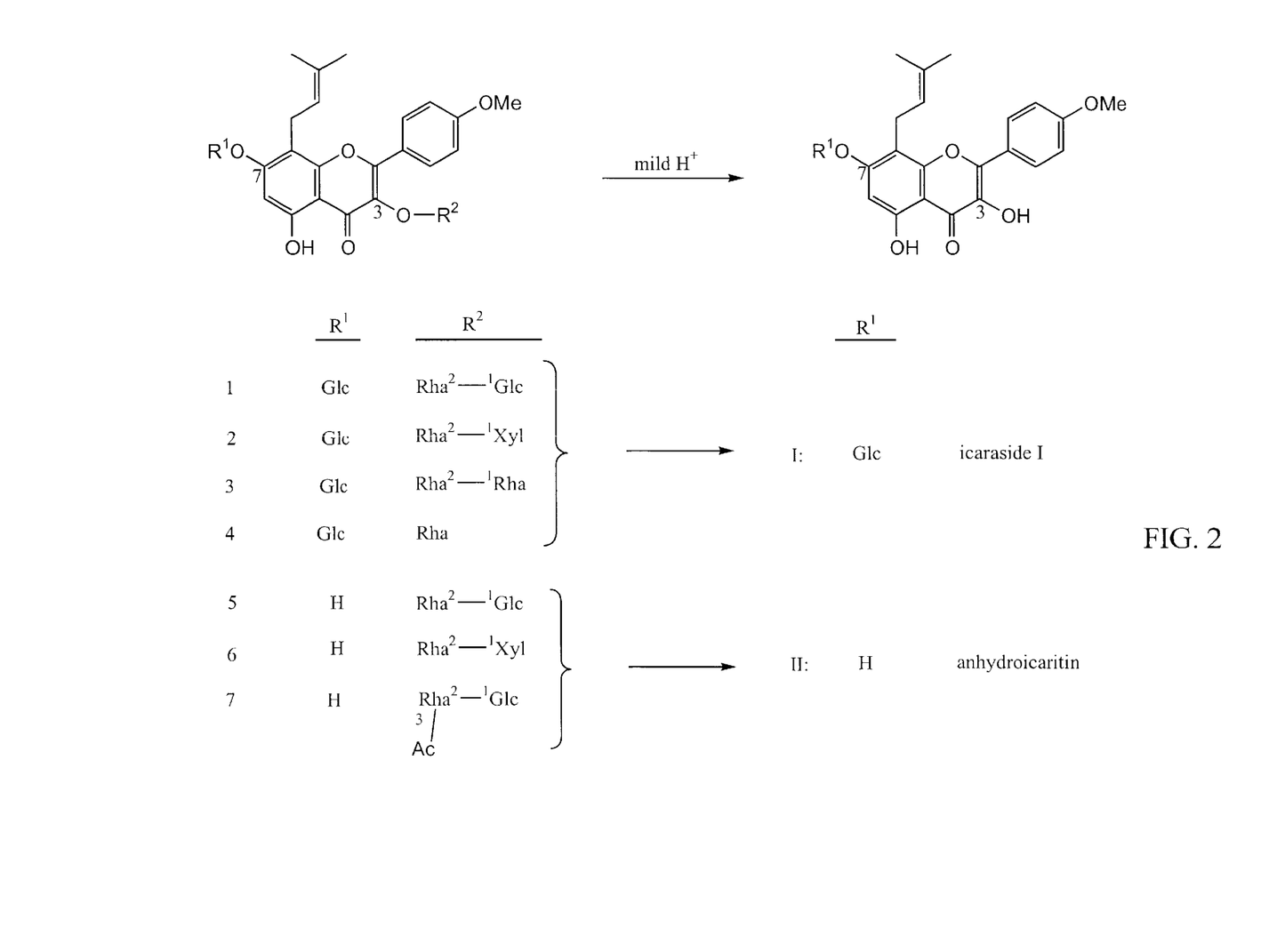
FIG. 2 shows the products formed after acid hydrolysis of the prenylated flavonol glycosides contained in Epimedium plants according to the method of this invention.

The process of this invention, as best illustrated in FIG. 2, is based on the discovery that substantially all of the Group I prenylated flavonol glycoside compounds 1–4 and their corresponding acetate derivatives contained in an Epimedium extract can be converted to a single compound, icariside I (compound I), by subjecting an Epimedium extract to acid hydrolysis, which surprisingly cleaves exclusively the sugar units at the 3-position of the Group I compounds such as the epimediums A, B, and C, icariin (FIG. 1, compounds 1–4), and their corresponding acetate derivatives, without cleaving the β-glucoside at position 7. The mild acid hydrolysis also cleaves all of the acetate groups on the acetate derivatives (not shown). The Group II prenylated flavonol glycosides such as sagittatosides A, B, and C (FIG. 1, compounds 5–7) and their corresponding acetate derivatives lack a 7-β-glucoside unit and therefore are converted to anhydroicaritin (compound II) upon hydrolysis of the 3-β-glucoside unit. Thus, the method of the invention produces a composition enriched in both icariside I and anhydroicaritin. The compositions obtained after purification of the acid hydrolysis compositions by methods described below in detail typically comprise between about 15–60% by weight icariside I and between about 2–12% by weight anhydroicaritin.

Figure 3:
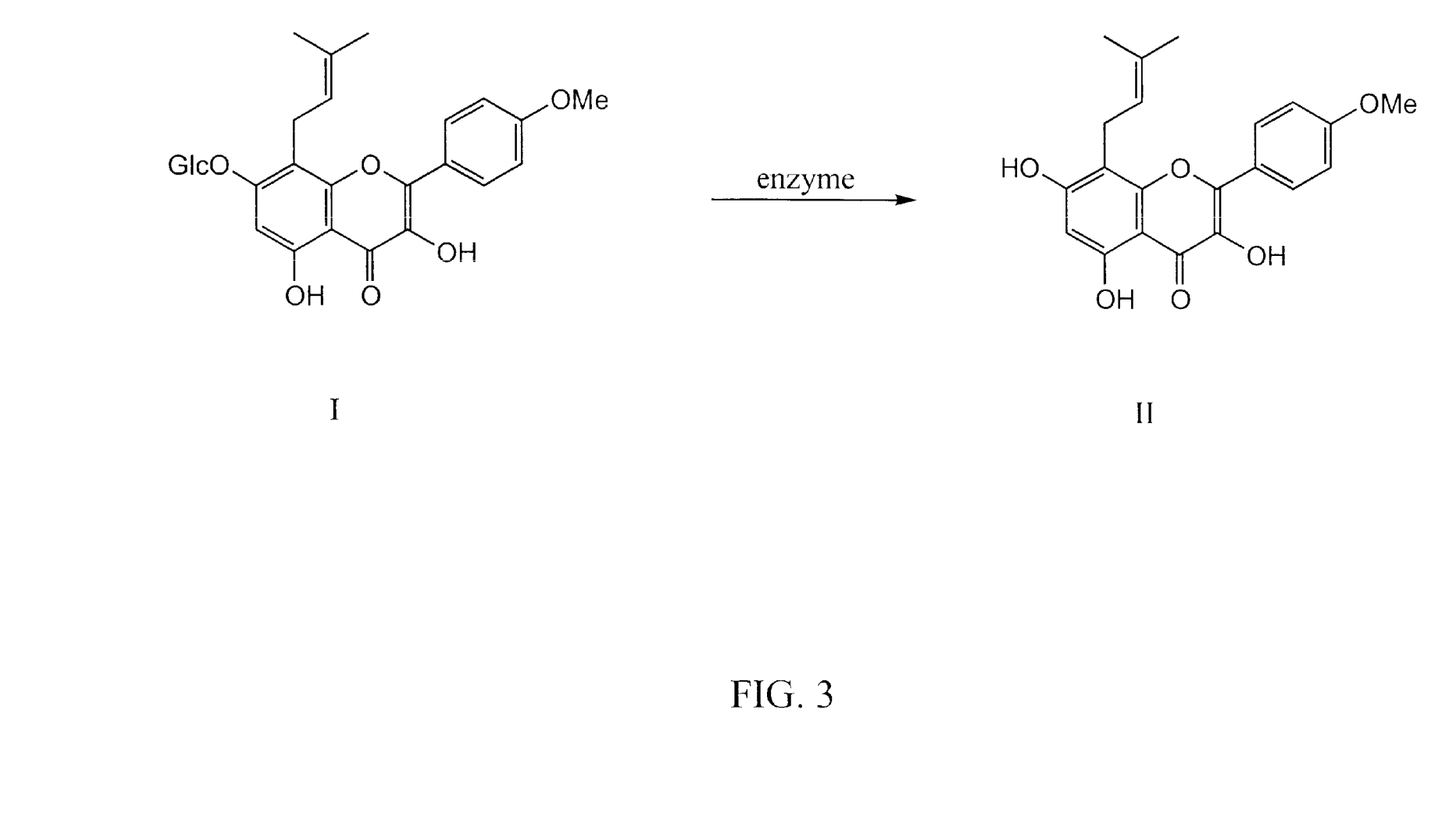
FIG. 3 illustrates the enzymatic method of this invention for converting icariside I to anhydroicaritin.

If a composition further enriched for anhydroicaritin (compound II) is desired, the above-described acid hydrolysis composition comprising a mixture of icariside I and anhydroicaritin can be subjected to enzymatic hydrolysis to convert substantially all of the icariside I to anhydroicaritin, as illustrated in FIG. 3.

A further surprising discovery of this invention is that icariside I was found to be a stronger inhibitor of the enzyme phosphodiesterase type V (PDE-5) than any of the individual PFG compounds 1–7 shown in FIG. 1 (crude or purified) or even a mixture of the PFG's contained in Epimedium plants. It was further discovered that anhydroicaritin is also a strong PDE-5 inhibitor. The term "PDE-5 inhibitor" as used herein is intended to mean an agent that is capable of inhibiting or selectively reducing the activity of PDE-5. Thus, the present invention provides novel PDE-5 inhibitor compositions. The compositions of this invention may contain icariside I, anhydroicaritin, or mixtures of icariside I and anhydroicaritin.

The process of this invention produces compositions comprising icariside I and/or anhydroicaritin from an Epimedium plant extract with the extraction of prenylated flavonol glycosides from an Epimedium plant. As used herein, the term "extract" is interchangeable with the term "Epimedium extract" and refers to a substance derived from an Epimedium plant source, including extracts prepared from the whole plant or from various parts of the plant, such as the leaves, stems, roots, etc. Thus, the method of this invention is not limited to the particular part of the plant used to prepare the extract. Examples of species within the Epimedium genus suitable for use in the present invention include, but are not limited to, *E. sagittatum, E. grandiflorum, E. brevicornum, E. acuminatum, E. baicaliquizhounense, E. baojingenensis, E. clongatum, E. caotum, E. davidii, E. ecalcaratum, E. fargesii, E. glandolospilosum, E. haiyangense, E. hunanense, E. leptorrhizum, E. koreanum, E. platypetalum, E. pubesens, E. reticulatum, E. simplicioflium, E. sutchuenense, E. truncatum, E. wushanense,* and *E. zushanense*. It is common practice in traditional Chinese medicine and in the literature for the species *E. sagittatum, E. grandiflorum,* and *E. brevicornum* to be used interchangeably. As such, the terms *E. sagittatum, E. grandiflorum,* and *E. brevicornum* will also be used interchangeably in the description of the present invention.

The extract is prepared by extracting the prenylated flavonol glycosides from an Epimedium plant into an appropriate solvent. The extract can be prepared by using the general methods described herein and other equivalent methods known in the art, such as soxhlet extraction, percolation, vat extraction, or countercurrent extraction. The degree of comminutation of the plant material prior to the extraction process should provide sufficient particulate surface area for the extraction solvent to contact. The particular method of extraction employed is not essential to the process of the present invention.

In a preferred embodiment, the extraction process is accomplished by placing the leaves, stems, or both or an Epimedium plant in a solvent such as water or an alcohol/water mixture at a temperature between room temperature and 90° C., with about 55° to 90° C. being preferred. Suitable alcohols for use in the extraction step include, but are not limited to, ethanol, methanol, and isopropyl alcohol. Preferably the extraction solvent comprises 0–95% ethanol in water, and more preferably the extraction solution comprises 0–50% ethanol in water. The amount of plant material to solvent mixture used in the extraction process varies between about 1:1 to about 1:20 on a gram to milliliter basis, with 1:5 being preferred. The plant material is contacted with the extraction solution until substantially all of the prenylated flavonol glycosides are extracted into the extraction solvent. Such a crude Epimedium extract typically contains epimediums A–C, icariin, sagittatosides A–C (FIG. 1) and their respective acetate derivatives, as well as other compounds present in the plant material. As will be understood by those of skill in the art, the relative amounts of compounds 1–7 shown in FIG. 1 will vary not only between different Epimedium plant genuses, but will also vary between extracts of the same species, with the exception of the species *E. sagittatum, E. grandiflorum,* and *E. brevicornum* as discussed above.

At this point, the crude extract may be used in its crude form in the acid hydrolysis step, or the crude extract can be purified as described in Example 9 to increase the percentage of PFG's in the extract. To purify the crude extract, the crude extract is combined with an extraction solvent such as acetone/water or ethanol/water. Preferably the solvent used to purify the extract is 80–85% acetone/water. The mixture of the crude extract and the extraction solvent is stirred for approximately 5 to 30 minutes. The solvent is then removed by decanting or filtration. If desired, the above-described extract purification steps may be repeated. As stated above, the purified extract obtained by the purification method of this invention may be used in the acid hydrolysis step described below, or alternatively the purified extract containing a higher percentage of PFG's may be used as a nutraceutical. For example, as will be discussed below in detail and shown in Table 1 below, compositions of this invention comprising high purity PFG's (i.e., at least 20% by weight PFG) were found to be potent inhibitors of PDE-5 activity.

The crude or purified extract is filtered, the extraction solvent is removed, and the crude extract is dried at room temperature or at an elevated temperature, either in a vacuum oven or at atmospheric pressure, prior to the acid hydrolysis step, discussed below in detail.

Alternatively, if the extraction solvent used during the extraction step is a high-alcohol content solvent (i.e., comprising between about 80–95% alcohol), the acid hydrolysis step can be carried out either on the crude extract without removing the extraction solvent, or on the dried extract as prepared as described above.

Figure 4:
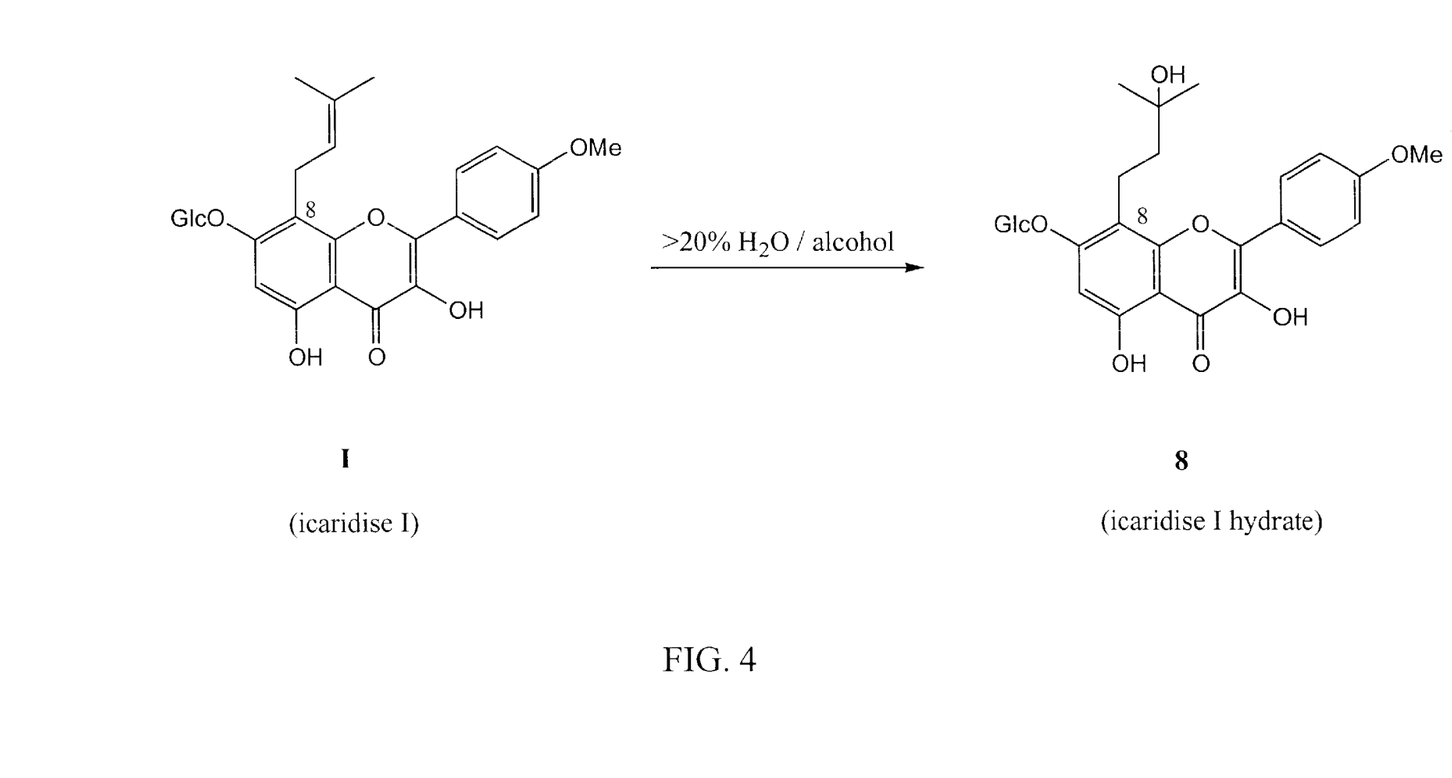
FIG. 4 shows the formation of icariside I hydrate from icariside I.

As shown in FIG. 2, the method of the invention for preparing compositions comprising icariside I and/or anhydroicaritin comprises subjecting a crude Epimedium plant extract to mild acid hydrolysis. If a dried Epimedium extract is utilized, the dried extract is dissolved in alcohol or an alcohol/water solution, preferably in 80–95% alcohol/water. Suitable alcohols for use as solvents in the acid hydrolysis step include, but are not limited to ethanol or methanol, with ethanol being preferred. Alternatively, an aqueous solution of 80–90% acetone may be used as the hydrolysis solvent. Regardless of the organic solvent used, it was surprisingly and unexpectedly discovered that in order to obtain a good recovery of the desired icariside I, the hydrolysis step should be performed in a hydrolysis solvent having a high alcohol or high acetone content. That is, that the ratio of the organic solvent (i.e., alcohol or acetone) to water in the hydrolysis solvent should be about at least 80:20 organic solvent/water. The inventors discovered that when the amount of water in the hydrolysis solvent was greater than 20%, some of the desired icariside I product became hydrolyzed during the hydrolysis step and produced significant amounts of the undesired hydrate (icariside I hydrate), shown as compound 8 in FIG. 4. The formation of the hydrate product of icariside I (compound 8) is undesirable in that icariside I hydrate was found to be essentially inactive in PDE-5 inhibition studies.

After addition of the hydrolysis solvent to the Epimedium extract to form an extract mixture, a strong mineral acid is added to the extract mixture. Preferably, the amount of acid added is approximately 350–1440 milliequivalents (mEq), preferably 540 mEq, of mineral acid per 100 grams of dried extract. Among the preferred mineral acids are sulfuric acid ($H_2SO_4$), hydrochloric acid (HCl), perchloric acid ($HClO_4$), hydrobromic acid (HBr), and nitric acid ($HNO_3$), with sulfuric acid being preferred. The aforementioned list is exemplary of the acids that may be used and is not meant to limit the scope of the present invention.

The acidic solution is heated to reflux for approximately 1 to 4 hours, or until substantially all of the compounds 1–4 (FIG. 1) and their corresponding acetate derivatives are hydrolyzed as determined by HPLC analysis. As discussed above, the inventors discovered that the mild acid hydrolysis conditions used in the method of this invention selectively hydrolyzed the saccharide and disaccharide moieties at the C-3 of compounds 1–7, without hydrolyzing the β-glucoside unit at C-7 of compounds 1–4 (FIG. 2). Consequently, epimediums A, B, and C, icariin, (compounds 1–4) and their corresponding acetate derivatives are all converted to icariside I. The sagittatosides (compounds 5–7), which lack a β-glucosyl moiety at the 3-position, are converted to anhydroicaritin under the above-described acid hydrolysis conditions.

The resulting crude hydrolyzate (i.e., the acid hydrolysis mixture) can be filtered to remove acid salts and other solids, and dried to provide a filtered hydrolyzate comprising about 5% by weight icariside I and 1.3% by weight anhydroicaritin. Preferably, the crude filtered hydrolyzate is purified, for example, by one of the methods described below to provide a higher purity icariside I-containing composition.

Figure 5:
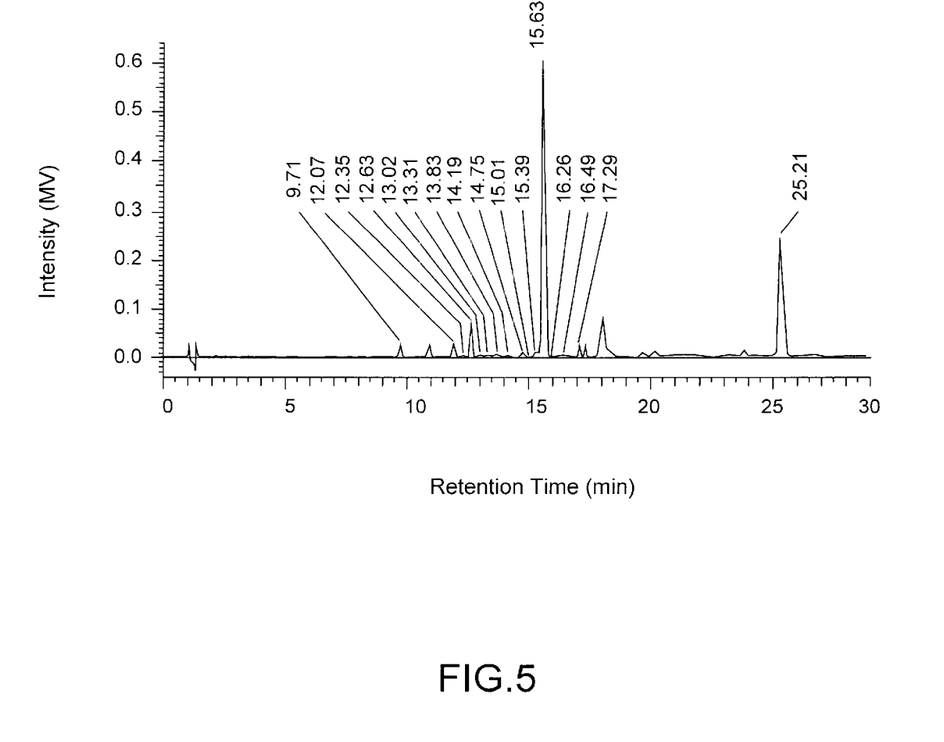
FIG. 5 shows an HPLC chromatogram of a composition produced after purification of an acid hydrolysis mixture by reversed phase chromatography as described in Example 1.

In one embodiment, a higher purity icariside I is obtained by purifying the crude filtered hydrolyzate mixture by column chromatography. In this embodiment, the crude filtered hydrolyzate mixture is diluted with water. The diluted filtrate is then loaded onto a column having an adsorbent capable of retaining icariside I while allowing unreacted PFG's, sugars and other polar materials to elute from the column. Preferably, the adsorbent is a reversed phase matrix, including, but not limited to, divinylbenzene-polystyrene copolymer, polymethacrylate, or octadecylsilane (C-18). Subsequent to loading the crude filtered hydrolyzate product onto the column, the unreacted PFG's, sugars and other polar materials that have little or no affinity for the adsorbent, are specifically washed from the column matrix using 40–60% ethanol. This wash is followed by a second wash with an organic solvent such as methanol, 95% ethanol, or acetone to elute the icariside I along with the anhydroicaritin, providing a composition comprising about 15 to 30% by weight icariside I and about 3.5 to 8% by weight anhydroicaritin. FIG. 5 illustrates a typical HPLC chromatogram of a composition of this invention isolated after the above-described column chromatography purification and as described in detail below in Example 1.

Figure 6:
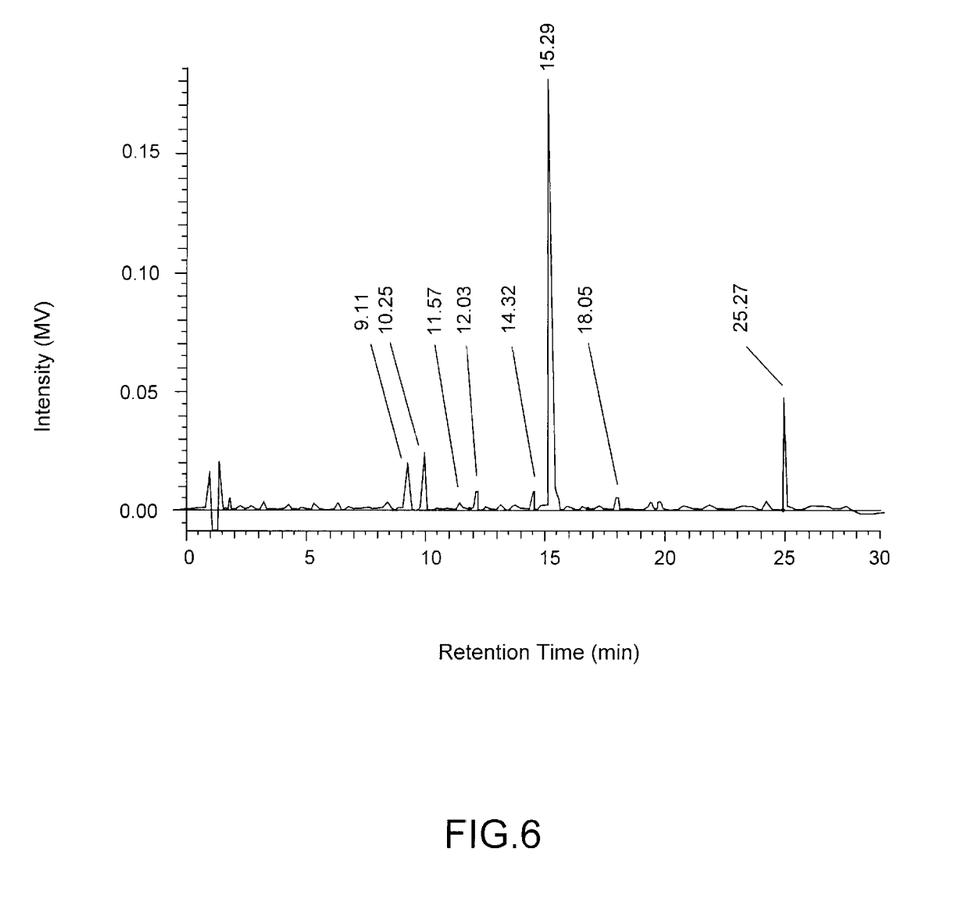
FIG. 6 shows an HPLC chromatogram of a composition produced after purification of an acid hydrolysis mixture by liquid/liquid extraction purification as described in Example 2.

In yet another embodiment, a higher purity icariside I is obtained by a liquid/liquid extraction method. In this embodiment, the crude filtered hydrolyzate mixture is diluted with water and neutralized with a base. Non-limiting bases suitable for neutralizing the acidic solution include sodium hydroxide (NaOH), potassium hydroxide (KOH), ammonium hydroxide ($NH_4OH$), sodium carbonate ($Na_2CO_3$), and sodium bicarbonate ($NaHCO_3$), with 50% (v/v) aqueous NaOH being preferred. The neutralized crude hydrolyzate is then extracted one or more times with a water-immiscible organic solvent such as ethyl acetate or n-butanol. The aqueous phase contains the undesired compounds such as unreacted PFG's, sugars, and other polar materials. The organic fractions, containing the desired acid hydrolysis compounds, are combined, concentrated and dried to provide a composition comprising about 15 to 30% by weight icariside I and about 3.5 to 8% by weight anhydroicaritin. FIG. 6 illustrates a typical HPLC chromatogram of a high purity icariside I composition isolated after the above-described precipitation method and as described in greater detail in Example 2.

Figure 7:
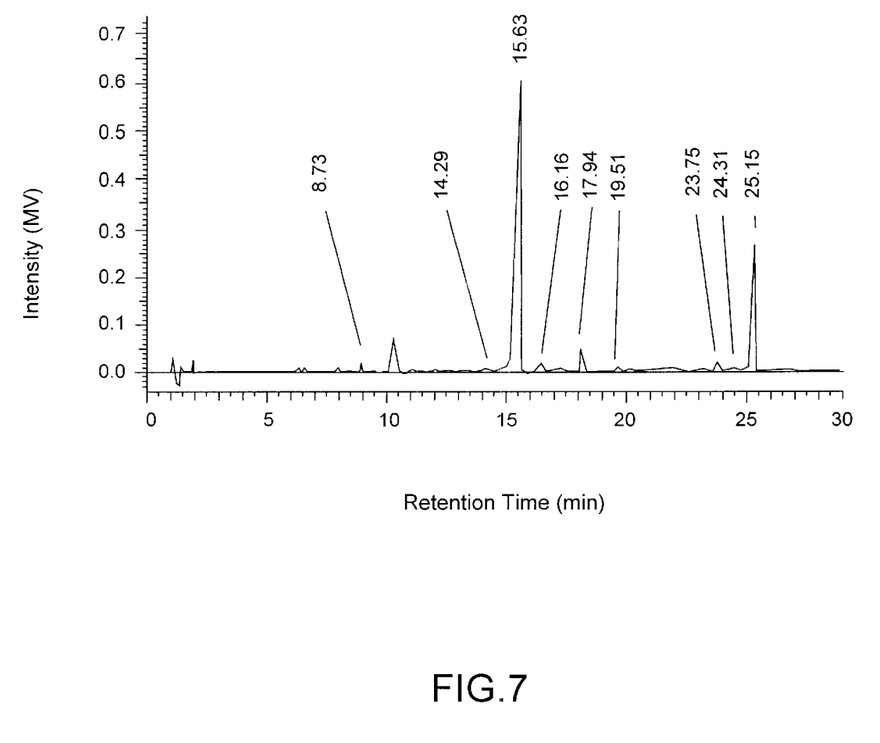
FIG. 7 shows an HPLC chromatogram of a composition produced after purification of an acid hydrolysis mixture by precipitation as described Example 3.
Figure 8:
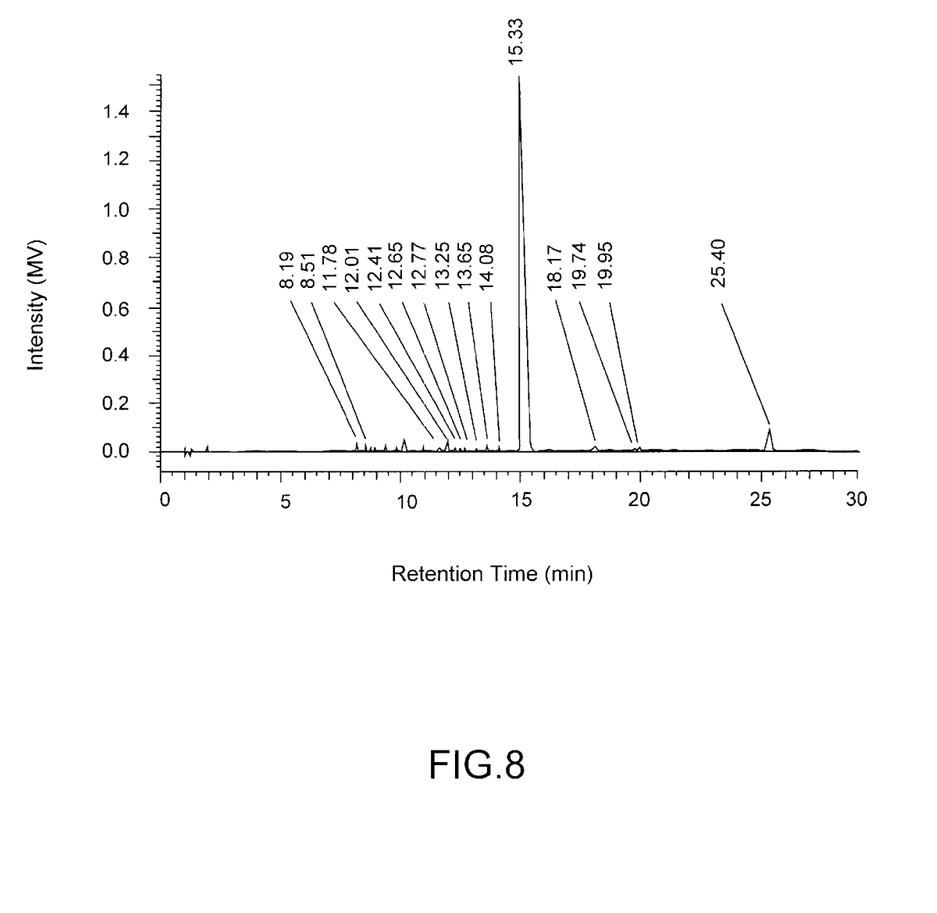
FIG. 8 shows an HPLC chromatogram of a composition produced after purification of an acid hydrolysis mixture by a precipitation method as described Example 4.

In yet another embodiment, a higher purity icariside I composition is obtained by a precipitation procedure in which the less water-soluble icariside I is recovered by filtration from a diluted and neutralized sample of the filtered hydrolyzate. In this embodiment, the acid in the filtered hydrolyzate is neutralized by adding a base such as sodium hydroxide (NaOH), potassium hydroxide (KOH), ammonium hydroxide ($NH_4OH$), sodium carbonate ($Na_2CO_3$), or sodium bicarbonate ($NaHCO_3$), with NaOH being preferred. However, it is to be understood that bases other than the aforementioned bases may be used to neutralize the solution. At this point, phosphoric acid is optionally added to the neutralized solution to add phosphates which help to solublize the non-icariside I solids and thus improve purity of the final composition. Next, water is added to the neutralized solution. Preferably, the amount of water added is 2.5 times the volume of filtered hydrolyzate solution, to cause the icariside I and anhydroicaritin to precipitate out of solution, and then pH of the solution is adjusted to pH 5–9, preferably pH 8–9, by the addition of one of the aforementioned bases, such as NaOH. The basic solution is then filtered to collect the icariside I solids. Alternatively, the basic solution is heated to 50–80° C. before filtration in order to aid in the coagulation of the fine icariside I precipitate and facilitate the filtration. The solids obtained by this precipitation method comprise about 15–60% by weight icariside I and about 3.5–20% anhydroicaritin. FIGS. 7 and 8 illustrate typical HPLC chromatograms of a high purity icariside I composition isolated after the above-described precipitation method and as described in greater detail in Examples 3 and 4.

As stated above, this invention is further directed to a method of preparing compositions enriched for anhydroicaritin. This is achieved by subjecting a crude or purified hydrolyzate, such as those described above comprising a mixture of icariside I and anhydroicaritin, to enzymatic hydrolysis, as illustrated in FIG. 3 and as described in detail in Example 5. Enzymes suitable for converting icariside I to anhydroicaritin include, but are not limited to, hesperidinase, lactase, β-glucosidase, pectinase, α-amylase, α-glucosidase, and β-amylase. The method generally comprises dissolving the crude or purified hydrolyzate in ethanol and water or buffer, adding dry enzyme to the solution, and heating the mixture to about 25° to 50° C., preferably at about 40° C., for an appropriate period of time. The enzymatic hydrolysis converts substantially all of the icariside I contained in the hydrolyzate to anhydroicaritin, thereby producing a composition enriched for anhydroicaritin.

The various icariside I and anhydroicaritin-containing compositions obtained by the methods of this invention, as well as crude or purified Epimedium extracts containing PFG's, were screened for their ability to inhibit PDE-5 as described in Hidaka, H. et al. (*Biochem. Biophys. Acta* (1976)429:428) and Nelson, C. D. (*Trends Pharmacol. Sci.* (1991) 12:19). The results of the PDE-5 inhibition assays of crude Epimedium extracts and of crude and purified hydrolyzates are summarized below in Tables 1 and 2.

Table 1 shows the $IC_{50}$'s obtained in PDE-5 inhibition assays for Epimedium extracts prepared by various methods. In particular, entries 5 and 6 in Table 1 show that compositions of this invention comprising at least 20% by weight of purified PFG's are potent inhibitors of PDE-5 activity. Thus, the present invention also comprises compositions having PDE-5 inhibition activity, wherein the compositions comprise at least 20% PFG's. Alternatively, the compositions of this invention comprising purified PFG's may also be combined with compositions of this invention comprising icariside I and/or anhydroicaritin, discussed below.

Table 2 shows the IC50's obtained in PDE-5 inhibition assays for compositions of this invention obtained after acid hydrolysis of Epimedium extracts, and compares these IC50's with the IC50 for sildenafil. Table 2 show that compositions of this invention comprising icariside I (entries 7–10) and anhydroicaritin (entry 11) possess significant inhibition of PDE-5, and further that the compositions of this invention comprising icariside I and anhydroicaritin are more potent inhibitors of PDE-5 than crude Epimedium extracts (Table 1). Even more significantly, the results shown in Table 2 illustrate that compositions of this invention comprising high amounts of icariside I or anhydroicaritin have PDE-5 inhibition activities approaching that of Viagra® (see for example entries 10 and 11 in Table 2). Currently, Viagra®, generically known as sildenafil, is the leading remedy for sexual dysfunction, in particular erectile dysfunction. It has been well established that sildenafil is a potent PDE-5 inhibitor, with an IC50 of 0.031 $\mu$g/mL (3.5 nM). While not wishing to be bound by any particular theory, the inventors presume that the PDE-5 inhibitors of this invention will act by a similar mechanism to in vitro Viagra® and therefore posses similar benefits for treating sexual dysfunction as Viagra®, but without the negative side-effects produced by Viagra®. Thus, the method of this invention provides a more natural alternative to Viagra® by providing a compositions comprising strong PDE-5 inhibitors, namely icariside I and anhydroicaritin. Based on a comparison of results obtained in studies of the PDE-5 inhibitor Viagra®, it is believed that there will be beneficial results with the compositions of this invention for female sexual dysfunction as well, and the composition will likely provide a remedy for many female conditions.

The present invention further provides improved formulations for modulating the human sexual response in a human by administering a composition of this invention in an amount effective to increase blood flow to the genitalia. According to the invention, modulation of male and female human sexual response is provided on demand by administering an effective amount, preferably by oral administration, of a composition of this invention. An effective amount of icariside I, anhydroicaritin, or mixtures of icariside I and anhydroicaritin obtained from any of the above-described procedures can be combined with one or more excipients to form a standardized composition (e.g., a pharmaceutical composition or a dietary supplement) for treating sexual dysfunction or maintaining sexual function in males and females. By an "effective" amount is meant a nontoxic but sufficient amount of a composition of this invention to provide the desired effect, for example, treatment of erectile dysfunction.

The terms "treating" and "treatment" as used herein refer to reduction in severity and/or frequency of symptoms, elimination of symptoms and/or underlying cause, and/or prevention of the occurrence of symptoms and/or their underlying cause. The present method of "treating" erectile dysfunction, as the term is used herein, thus encompasses both prevention of the disorder in a predisposed individual and treatment of the disorder in a clinically symptomatic individual.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising", "include," "including," and "includes" when used in this specification and in the following claims are intended to specify the presence of stated features, integers, components, or steps, but they do not preclude the presence or addition of one or more other features, integers, components, steps, or groups thereof.

EXAMPLES

Example 1

Acid Hydrolysis of a 50% EtOH Extract and Purification by Reversed Phase Chromatography Whole *Epimedium grandiflorum* leaves were extracted with a 1:1 mixture of ethanol and water at 55° C. The resulting extract (referred to as a "50% EtOH extract") was filtered and the filtrate concentrated at 40–50° C. under vacuum and then dried under vacuum at 60° C. to a dry solid. The dried extract (131 g) containing approximately 5.8 g of total PFG's was placed in a 2 liter round bottom flask and 1 L of 90% ethanol was added. The mixture was heated to reflux to help dissolve the solids. Concentrated sulfuric acid (28 mL) was added. The mixture refluxed for 2 hr, cooled to room temperature, and 900 mL of water added with stirring. Next the mixture was filtered using vacuum to remove insoluble sulfate salts and other solids and loaded on a 2.5×56 cm (275 mL) column packed with 250–600 micron divinylbenzene cross-linked polystyrene resin (Mitsubishi Chemical). The column was washed with 2 column volumes (CVs) of 60% ethanol and the icariside I was eluted with 2 CVs of 95% ethanol. The product pool was air-dried producing 11.3 g of brown solids. HPLC analysis (FIG. 5) showed that the solids contained 18% icariside I (peak 15.27 min) and 12% anhydroicaritin (peak 25.15 min). The recovery of the icariside I in the product pool was 87% of the amount present in the hydrolyzate.

Example 2

Purification of a Hydrolyzate by Liquid/liquid Extraction

The ethanolic hydrolyzate (25 mL) prepared in Example 1 was mixed with 62.5 mL of de-ionized water and the pH was adjusted to 7.0 using 50% (w/w) sodium hydroxide solution. The resulting mixture was extracted with three 25 mL portions of ethyl acetate and the combined ethyl acetate extracts were back extracted with 150 mL of water. The ethyl acetate layers were combined, dried, and assayed for icariside I. HPLC analysis (FIG. 6) showed that the dried EtOAc fractions contained 22% icariside I (peak 15.29 min) and 11% anhydroicaritin (peak 25.27 min), and icariside I recovery into the ethyl acetate was 97% of the amount present in the hydrolyzate. The partition coefficient for icariside I between ethyl acetate and water was found to be 16, indicating that the icariside I has a high affinity for ethyl acetate over water.

Example 3

Acid Hydrolysis of a 50% EtOH Extract and Purification by Precipitation

The dried extract (204 g) described in Example 1 was mixed with 1 L of 90% EtOH and then heated to reflux to help dissolve the solids. Sulfuric acid (25 ML) was added slowly with swirling. The mixture was refluxed 90 minutes and immediately chilled to stop the reaction. After cooling to room temperature, the mixture was filtered under reduced pressure through cellulose paper to remove insoluble sulfates and other materials, and the cake was washed with about 350 mL of 90% ethanol. The resulting ethanolic hydrolyzate (1.34 L) contained 4.1 g of icariside I.

The ethanolic hydrolyzate prepared above (1.32 L) was placed in a 10 L container and 40 g of 50% (w/w) sodium hydroxide solution was added followed by 20 mL of phosphoric acid. Next 3.3 L of deionized water was added with stirring. The pH of this mixture was 2.4. Sodium hydroxide solution (50% w/w) was added until the pH was 8.25. The mixture was heated to 65° C. to assist with the coagulation of the precipitate. The mixture was cooled to room temperature and stirred for 0.5 hr at room temperature before filtering through a cellulose filter using vacuum. The resulting brown solids were washed with 715 mL of 10% ethanol and dried either under vacuum at room temperature or in air at 55° C. to yield brown solids. HPLC analysis (FIG. 7) showed the solids contained 20% icariside I (peak 15.27 min) and 10% anhydroicaritin. Recovery of icariside I using this precipitation procedure was 94% of the amount present in the hydrolyzate.

Example 4

Acid Hydrolysis of a Water Extract and Purification by Precipitation

Ground *Epimedium grandiflorum* leaves (0.40 kg) were mixed with 5 L water in a 10 L round bottom flask. The flask was placed on a rotary evaporator for two hours at a rotation speed of 120 rpm and a water bath temperature of 90° C. The extract was filtered under reduced pressure through cellulose paper. The resulting filtrate (3.2 L) was evaporated using the rotary evaporator to a volume of 100 mL and dried under vacuum at 50° C.

The dark brown solids prepared above (40.4 g) were mixed with 200 mL of 90% ethanol and 6.0 mL of sulfuric acid in a 500 mL round bottom flask. The mixture was refluxed for 90 minutes and immediately chilled to stop the reaction. This mixture was filtered under reduced pressure through cellulose paper to remove insoluble sulfates and other materials. The cake was washed with 15 mL of 90% ethanol. The resulting ethanolic hydrolyzate (215 mL) contained 0.53 g of icariside I.

The hydrolyzate prepared above (50 mL) was transferred to a 250 mL beaker and 2.5 mL of 50% (w/w) sodium hydroxide solution was added with stirring to adjust the pH of the solution to pH 9, followed by 1.5 mL of concentrated phosphoric acid. Deionized water (125 mL) was added, and the mixture was adjusted to pH 8.2 using 1.5 mL of 50% sodium hydroxide solution. The mixture was heated to 65° C. to assist with coagulation of the precipitate and cooled to room temperature. The mixture was allowed to sit undisturbed at room temperature for 30 minutes prior to filtration under reduced pressure through cellulose paper. The resulting olive-green solids were washed with 25 mL of de-ionized water and dried under vacuum at room temperature or in air at 80° C. to produce olive-green solids. HPLC analysis (FIG. 8) showed the solids contained 60% icariside I (peak 15.33 min) and 2.4% anhydroicaritin (peak 25.40 min). Recovery of icariside I using this precipitation procedure was 92% of the amount present in the hydrolyzate.

Example 5

Enzymatic Hydrolysis of Icariside I a) The substrate was a partially purified icariside I product with 20% icariside I and 11% anhydroicaritin. About 50 mg was dissolved in 10 mL of ethanol, and water or buffer was added until the mixture became cloudy (about 20% ethanol). The following dry enzymes were added to separate samples: α-amylase, α-glucosidase, β-amylase, β-glucosidase, hesperidinase, lactase, and pectinase. The samples were incubated overnight at 40° C. and analyzed by HPLC. The results were only semi-quantitative due to the difficulty in dissolving the anhydroicaritin that precipitated from the samples. However, several of the chromatograms did show a definite reduction in icariside I and increase in the ratio of anhydroicaritin to icariside I. The best results were obtained using hesperidinase, lactase, β-glucosidase and pectinase.

A larger scale experiment was done using hesperidinase in order to isolate pure anhydroicaritin for characterization. Pure icariside I (20 mg) was dissolved in 10 mL of ethanol and 50 mL of water and 200 mg of hesperidinase enzyme was added and the mixture was incubated for 24 hr at 40° C. Crude anhydroicaritin was collected via filtration and purified on a 2.5×30 cm semi-prep C-18 HPLC column using a gradient of 50:50 (MeCN/H$_2$O) to 80:20 (MeCN/H$_2$O) in 20 min. The pure anhydroicaritin was analyzed by LC/MS and proton NMR.

b) Enzymatic Hydrolysis of PFG's: The purified PFG solids (55.3%, purified by reversed-phase chromatography of a 50% EtOH extract) were subjected to enzymatic hydrolysis with the same enzymes and conditions described in part (a). Hesperidinase, lactase, β-glucosidase and pectinase appeared to convert the mixture of PFG's to a mixture of sagittatosides, but no icariside I or anhydroicaritin were observed. This indicated that these enzymes were specific for the 7-β-glucosyl group and did not hydrolyze the 3-position sugar(s).

Example 6

Preparation of a High Anhydroicaritin-containing Product

A high sagittatosides *Epimedium sagittatum* extract containing 24.7% total sagittatosides (assayed as icariin) and 8.1% icariin and other expected prenylated flavonol glycosides was obtained from China. A 50 g portion of this extract was mixed with 250 mL of 90% ethanol and 7.5 mL of concentrated sulfuric acid in a 500 mL round bottom flask. The mixture was refluxed for 90 minutes, then allowed to cool to room temperature. The hydrolyzed mixture was filtered under reduced pressure through cellulose paper to remove insoluble sulfates and other materials. The cake was washed with approximately 20 mL of 90% ethanol. The resulting filtered ethanolic hydrolyzate (305 mL) contained 3.75 g of anhydroicaritin and 2.50 g of icariside I.

The filtered hydrolyzate prepared above (200 mL) was transferred to a 1000 mL container and 8.0 mL of 50% (w/w) sodium hydroxide solution was added with stirring, followed by 4.0 mL of phosphoric acid. De-ionized water (500 mL) was then added. This mixture was adjusted to pH 4.9 using 50% sodium hydroxide solution. The mixture was allowed to sit undisturbed at room temperature for 24 hours prior to decanting off the liquid. The resulting solids were macerated using de-ionized water and filtered under reduced pressure through cellulose paper. The resulting dark brown solids (11.9 g) were washed with de-ionized water and dried in air overnight. The dark brown solids contained 20% anhydroicaritin and 12% icariside I and an anhydroicaritin/icariside I ratio of 1.66. The recovery of anhydroicaritin in the precipitation procedure was 94% from the hydrolyzate.

Example 7

Recrystallization of Icariside I

Icariside 1 (30 mg) obtained by a method described in Example 1 was dissolved in a minimum of hot tetrahydrofuran (THF). Hot methanol (approximately 10 mL) was then added. The hot THF/MeOH solution was filtered through a PTFE filter into a vial and allowed to evaporate at room temperature to about 5 mL, whereupon crystals began to form, and then placed in a 4° C. refrigerator for 24 hours. The crystals were filtered and washed with cold methanol and dried in a vacuum. Icariside I (21 mg) was isolated as yellow crystals and had a chromatographic purity of 97.4%.

Example 8

Large Scale Acid Hydrolysis of an Epimedium extract

An 800 g portion of an *Epimedium sagittatum* powder extract obtained from China containing about 13% total prenylflavonol glycosides as icariin was mixed with 4.0 L of 90% ethanol and 120 mL of sulfuric acid in a 10 L round bottom flask. The mixture was refluxed for 90 minutes and immediately chilled to stop the reaction. This mixture was filtered under reduced pressure through cellulose paper to remove insoluble sulfates and other materials. The cake was washed with approximately 200 mL of 90% ethanol. The resulting ethanolic hydrolyzate (4.0 L) contained 33.7 g of icariside I.

The ethanolic hydrolyzate prepared above was transferred to a 34 L container and 200 mL of 50% (w/w) sodium hydroxide solution was added with stirring, followed by 120 mL of phosphoric acid. De-ionized water (10 L) was then added. This mixture was adjusted to pH 8.2 using 120 mL of 50% sodium hydroxide solution. The mixture was stirred for 10 minutes and allowed to sit undisturbed at room temperature for 60 minutes prior to filtration under reduced pressure through cellulose paper. The resulting olive-green solids were washed with 750 mL of de-ionized water and dried under vacuum at 50° C. or in air at 80° C. The olive-green solids contained 44.6% icariside I. Recovery of icariside I in the precipitation procedure was 96% from the hydrolyzate.

Example 9

Large Scale Purification of an Epimedium Extract Containing Prenylflavonoid Glycosides A 3.7 kg portion of an *Epimedium sagittatum* powdered extract obtained from China containing approximately 10% total prenylflavonol glycosides (PFG's) assayed as icariin was stirred with 35 L of 85/15 acetone/water (v/v) in a 50 L mixing tank. The mixture was stirred vigorously for 30 minutes and allowed to sit for 5 minutes. The acetone extract layer (36 L) was decanted from the tank and contained 362 g of PFG's. Recovery of the PFG's in this extraction procedure was 96%.

A portion (about 500 mL) of the acetone extract was dried under reduced pressure at 50° C. or less, providing 16.1 g of brown solids which were analyzed to contain 28.6% total PFG's when assayed as icariin.

TABLE 1

| Entry | Sample description | % PFG's | PDE-5 IC$_{50}$ (µg/mL) |
|---|---|---|---|
| 1 | Vat extraction of Epimedium leaves, refluxing for 17 hours with methanol | 8.0 | 5.78 |
| 2 | Extract prepared by extracting Epimedium leaves with 50% ethanol | 7.2 | 4.24 |
| 3 | Extract prepared by extracting Epimedium leaves with 90% ethanol | 10.2 | 12.50 |
| 4 | Extract prepared by extracting Epimedium leaves with 50% EtOH and then purifying the extract (after removal of EtOH) by liq/liq extraction with butanol. Sample tested was the butanol fraction. | 16.30 | 5.27 |

TABLE 1-continued

| Entry | Sample description | % PFG's | PDE-5 IC$_{50}$ ($\mu$g/mL) |
|---|---|---|---|
| 5 | Extract prepared by extracting Epimedium leaves with 50% EtOH and purifying by liquid/liquid extraction. Sample tested was the aqueous fraction of the liq/liq extraction. | 19.3 | 3.97 |
| 6 | Purification of a 90% ethanol extract on a HP-20 reversed phase column | 65.60 | 1.87 |

TABLE 2

| Entry | Sample description | % icariside I | PDE-5 IC$_{50}$ ($\mu$g/mL) |
|---|---|---|---|
| 7 | Crude hydrolyzate composition obtained from a 50% EtOH extract of Epimedium leaves | 2.1 | 24.30 |
| 8 | Crude hydrolyzate composition obtained from a 90% EtOH extract of Epimedium leaves | 5.3 | 9.39 |
| 9 | Icariside I fraction obtained from purifying hydrolyzate Sample No. 7 on a SP-70 reversed-phase column and eluting icariside I with alcohol | 21.4 | 1.50 |
| 10 | Pure (recrystallized) icariside I | 100 | 0.33 |
| 11 | Pure anhydroicaritin | 0 | 1.50 |
| 12 | icariside I hydrate | 0 | 21.50 |
| 13 | sildenafil | 0 | 0.031 |

We claim:

1. A method of producing a composition comprising at least 4% by weight icariside I, said method comprising:
   a) providing an extract of a plant of the genus Epimedium;
   b) adding a solvent and a mineral acid to said extract to form an extract mixture; and
   c) heating said extract mixture to provide a composition comprising at least 4% by weight icariside I.

2. The method of claim 1, wherein said composition further comprises between about 3 to 20% by weight anhydroicaritin.

3. The method of claim 1, wherein said extract comprises a first group of prenylated flavonol glycosides having a glycoside unit at the 3-hydroxyl position and a glycoside unit at the 7-hydroxyl position.

4. The method of claim 3, wherein said extract further contains one or more acetate derivatives of said first group of prenylated flavonol glycosides.

5. The method of claim 3, wherein the 3-position glycoside unit of each of said first group of prenylated flavonol glycosides is cleaved during said heating, whereby each of said first group of prenylated flavonol glycosides is converted to icariside I.

6. The method of claim 4, wherein said acetate derivatives are hydrolyzed to icariside I.

7. The method of claim 1, wherein said solvent comprises between 85 to 95% alcohol in water.

8. The method of claim 1, wherein said alcohol is ethanol or methanol.

9. The method of claim 1, wherein said mineral acid is selected from the group consisting of sulfuric acid, hydrochloric acid, perchloric acid, hydrobromic acid, and nitric acid.

10. The method of claim 1, wherein said heating comprises heating said extract solution at a temperature of between room temperature and 90° C.

11. The method of claim 1, wherein said plant is selected from the group consisting of E. sagittatum, E. brevicornum, E. grandiflorum, E. acuminatum, E. baicaliquizhounense, E. baojingenensis, E. clongatum, E. caotum, E. davidii, E. ecalcaratum, E. fargesii, E. glandolospilosum, E. haiyangense, E. hunanense, E. leptorrhizum, E. koreanum, E. platypetalum, E. pubesens, E. reticulatum, E. simplicioflium, E. sutchuenense, E. truncatum, E. wushanense, and E. zushanense.

12. The method of claim 11, wherein said plant is E. sagittatum, E. brevicornum, or E. grandiflorum.

13. The method of claim 1, wherein said plant extract is prepared by contacting all or a portion of a plant of the genus Epimedium with an extraction solvent comprising between zero to 95% alcohol in water.

14. The method of claim 13, wherein said extraction solvent comprises between zero and 50% alcohol in water.

15. The method of claim 13, wherein said portion of said plant comprises the leaves of said plant.

16. The method of claim 1, wherein said extract is a dried extract.

17. A composition comprising at least 15% by weight icariside I, prepared according to the method of claim 1.

18. A method of isolating a composition comprising at least 15% by weight icariside I, said method comprising:
   a) providing an extract of a plant of the genus Epimedium;
   b) adding a solvent and a mineral acid to said extract to form an extract mixture;
   c) heating said extract mixture to provide a hydrolyzate comprising at least 4% icariside I; and
   d) purifying said hydrolyzate to provide a composition comprising at least 15% icariside I.

19. The method of claim 18, wherein said composition further comprises between 3.5 and 20% anhydroicaritin.

20. The method of claim 18, wherein said purifying comprises:
   a) loading said hydrolyzate onto a column containing a polymer capable of retaining said icariside I;
   b) washing said column with a first solvent to remove unbound compounds with icariside I remaining adsorbed to the adsorbent; and
   c) eluting said icariside I from the adsorbent with a second solvent to obtain a composition comprising at least 15% by weight icariside I.

21. The method of claim 20, wherein said polymer is a reversed-phase matrix.

22. The method of claim 21, wherein said reversed-phase matrix is selected from the group consisting of divinylbenzene-polystyrene copolymer, polymethacrylate, and octadecylsilane.

23. The method of claim 20, wherein said first solvent is 40–60% ethanol.

24. The method of claim 20, wherein said second solvent is selected from the group consisting of methanol, 95% ethanol, and acetone.

25. The method of claim 18, wherein said purifying comprises:
   a) neutralizing said hydrolyzate with a base;
   b) extracting said neutralized hydrolyzate with a water-immiscible organic solvent to provide an organic layer containing said icariside I; and
   c) concentrating said organic layer to provide a composition comprising at least 15% by weight icariside I.

26. The method of claim 25, wherein said base is selected from the group consisting of sodium hydroxide, potassium hydroxide, ammonium hydroxide, sodium carbonate, and sodium bicarbonate.

27. The method of claim 25, wherein said base is 1:1 sodium hydroxide/water.

28. The method of claim 25, wherein said organic solvent is ethyl acetate or butanol.

29. The method of claim 18, wherein said purifying comprises:
   a) neutralizing said hydrolyzate with a base;
   b) adding phosphoric acid;
   c) adding water to precipitate solids containing icariside I;
   d) adjusting the pH of the composition of step (c) to between about 5–9;
   e) filtering said composition from step (d) to collect said composition comprising at least 15% by weight icariside I.

30. The method of claim 29, wherein said base is selected from the group consisting of sodium hydroxide, potassium hydroxide, ammonium hydroxide, sodium carbonate, and sodium bicarbonate.

31. The method of claim 29, wherein said pH is adjusted by adding a base selected from the group consisting of sodium hydroxide, potassium hydroxide, ammonium hydroxide, sodium carbonate, and sodium bicarbonate.

32. The method of claim 29, further comprising heating the composition from step (d) to a temperature between about 55–80° C.

33. A composition comprising at least 15% by weight icariside I, prepared according to the method of claim 18.

34. A method of producing a composition enriched for anhydroicaritin from a plant of the genus Epimedium, said method comprising:
   a) preparing an extract of said Epimedium plant;
   b) adding a solvent and a mineral acid to said extract to form an extract mixture;
   c) heating said extract mixture to provide a hydrolyzate comprising icariside I and anhydroicaritin; and
   d) subjecting said hydrolyzate to an enzymatic hydrolysis to convert said icariside I to anhydroicaritin, thereby producing a composition enriched for anhydroicaritin.

35. The method of claim 34, wherein said extract comprises a first group of prenylated flavonol glycosides having a glycoside unit at the 7-position and a glycoside unit at the 3-position, and a second group of prenylated flavonol glycosides having a hydroxyl unit at the 7-position and a glycoside unit at the 3-position.

36. The method of claim 35, wherein said first group comprises one or more prenylated flavonol glycosides selected from the group consisting of epimedium A, epimedium B, epimedium C, icariin, and acetate derivatives thereof, and wherein said second group comprises one or more prenylated flavonol glycosides selected from the group consisting of sagittatoside A, sagittatoside B, sagittatoside C, and acetate derivatives thereof.

37. The method of claim 35, wherein substantially all of said prenylated flavonol glycosides in said first group are hydrolyzed to icariside I during said heating.

38. The method of claim 35, wherein substantially all of said prenylated flavonol glycosides in said second group are hydrolyzed to anhydroicaritin during said heating.

39. The method of claim 35, wherein said enzyme is selected from the group consisting of α-amylase, α-glucosidase, β-amylase, β-glucosidase, hesperidinase, lactase, and pectinase.

40. A composition comprising at least 20% by weight icariside I.

41. The composition of claim 40, comprising between about 20–100% by weight icariside I.

42. The composition of claim 40, comprising at least 60% by weight icariside I.

43. The composition of claim 40, further comprising at least 3.5% by weight anhydroicaritin.

44. The composition of claim 43, comprising at least 5.5% by weight anhydroicaritin.

45. A PDE-5 inhibitor composition comprising at least 15% by weight icariside I.

46. The composition of claim 45, comprising between about 20–100% by weight icariside I.

47. A PDE-5 inhibitor composition comprising at least 3.5% by weight anhydroicaritin.

48. The composition of claim 47, comprising at least 5.5% by weight anhydroicaritin.

49. A method for treating sexual dysfunction, comprising administering to a subject an effective amount of a composition comprising at least 15% by weight icariside I.

50. The method of claim 49, wherein said composition comprises between about 20–100% by weight icariside I.

51. The method of claim 49, wherein said composition is formed as a pill for oral administration.

52. The method of claim 51, wherein said composition is formed as a pill for oral administration.

53. A method for treating sexual dysfunction, comprising administering to a subject an effective amount of a composition comprising at least 3.5% by weight anhydroicaritin.

54. The method of claim 53, wherein said composition comprises between about 20–100% by weight anhydroicaritin.

55. A composition for maintaining normal sexual function, comprising administering to a subject an effective amount of a composition comprising at least 15% by weight icariside I.

56. A method for maintaining normal sexual function, comprising administering to a subject an effective amount of a composition comprising at least 3.5% by weight anhydroicaritin.

57. A PDE-5 inhibitor composition comprising at least 20% by weight purified prenylated flavonol glycosides.

58. The composition of claim 57, comprising between about 20–66% purified prenylated flavonol glycosides.

59. A PDE-5 inhibitor composition comprising icarisid I and at least 20% by weight purified prenylated flavonol glycosides.

60. A method for treating sexual dysfunction, comprising administering to a subject an effective amount of a composition comprising at least 20% by weight purified prenylated flavonol glycosides.

61. A method for treating sexual dysfunction, comprising administering to a subject an effective amount of a composition comprising icarisid I and at least 20% by weight purified prenylated flavonol glycosides.

62. A method of producing a composition comprising at least 4% by weight icariside I, said method comprising:
   a) providing an extract of a plant of the genus Epimedium, wherein said extract comprises of prenylated flavonol glycosides having a glycoside unit at the 3-hydroxyl position and a glycoside unit at the 7-hydroxyl position;
   b) adding a solvent and a mineral acid to said extract to form an extract mixture; and
   c) heating said extract mixture, wherein the 3-position glycoside unit of each of said prenylated flavonol glycosides is cleaved during said heating, whereby each of said prenylated flavonol glycosides is converted to icariside I to produce a composition comprising at least 4% by weight icariside I.

63. The method of claim 62, further comprising purifying the composition isolated in step (c) to provide a composition comprising at least 15% icariside I.

64. A method of producing a composition enriched for anhydroicaritin from a plant of the genus Epimedium, said method comprising:
   a) preparing an extract of said Epimedium plant, wherein said extract comprises a first group of prenylated flavonol glycosides having a glycoside unit at the 7-position and a glycoside unit at the 3-position, and a second group of prenylated flavonol glycosides having a hydroxyl unit at the 7-position and a glycoside unit at the 3-position;
   b) adding a solvent and a mineral acid to said extract to form an extract mixture;
   c) heating said extract mixture, wherein substantially all of said prenylated flavonol glycosides in said first group are hydrolyzed to icariside I during said heating, to provide a hydrolyzate comprising icariside I and anhydroicaritin; and
   d) subjecting said hydrolyzate to an enzymatic hydrolysis to convert said icariside I to anhydroicaritin, thereby producing a composition enriched for anhydroicaritin.

* * * * *